(12) United States Patent
Roberts et al.

(10) Patent No.: US 9,067,024 B2
(45) Date of Patent: Jun. 30, 2015

(54) SAFETY DEVICE FOR A PRE-FILLED SYRINGE AND INJECTION DEVICE

(75) Inventors: Gareth Roberts, Wrexham (GB); Sioned Owen, Denbigh (GB); Matthew Ekman, Macclesfield (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 38 days.

(21) Appl. No.: 13/807,045

(22) PCT Filed: Jun. 21, 2011

(86) PCT No.: PCT/EP2011/060322
§ 371 (c)(1),
(2), (4) Date: Apr. 29, 2013

(87) PCT Pub. No.: WO2012/000838
PCT Pub. Date: Jan. 5, 2012

(65) Prior Publication Data
US 2013/0204196 A1    Aug. 8, 2013

(30) Foreign Application Priority Data

Jul. 2, 2010 (EP) .................................. 10168322

(51) Int. Cl.
*A61M 5/00* (2006.01)
*A61M 5/32* (2006.01)
(Continued)

(52) U.S. Cl.
CPC ......... *A61M 5/3202* (2013.01); *A61M 5/31568* (2013.01); *A61M 5/3157* (2013.01);
(Continued)

(58) Field of Classification Search
CPC ..... A61M 5/24; A61M 5/322; A61M 5/3202;
A61M 5/3234; A61M 5/3243; A61M 5/3271;
A61M 5/508; A61M 5/31551; A61M 5/31511;
A61M 15/009; A61M 15/0091; A61M 2015/0068
USPC ......... 604/192, 198, 211, 218, 219, 232, 110;
128/200.23; 222/36
See application file for complete search history.

(56) References Cited

U.S. PATENT DOCUMENTS 5,498,243 A * 3/1996 Vallelunga et al. ........... 604/197
6,454,743 B1 * 9/2002 Weber ............................ 604/131
(Continued)

FOREIGN PATENT DOCUMENTS

EP            1743666        1/2007
WO        2007/077463        7/2007

OTHER PUBLICATIONS

International Search Report for Int. App. No. PCT/EP2011/060322, completed Jan. 26, 2012.
(Continued)

*Primary Examiner* — Scott Medway
(74) *Attorney, Agent, or Firm* — McDonnell Boehnen Hulbert & Berghoff LLP

(57) ABSTRACT

A safety device for a pre-filled syringe comprises a hollow support body to retain the pre-filled syringe, a retaining collar and a rotating collar arranged within the support body. The retaining collar is releasably mounted to the support body. The rotating collar is slidable along an axial length of the support body and rotatable around a central axis of the safety device. The retaining collar is movable with respect to the support body in a proximal direction when the retaining collar is released from being mounted to the support body by the rotating collar.

15 Claims, 7 Drawing Sheets

(51) Int. Cl.
*A61M 5/315* (2006.01)
*A61M 5/50* (2006.01)

(52) U.S. Cl.
CPC ............ *A61M 5/326* (2013.01); *A61M 5/3287* (2013.01); *A61M 5/502* (2013.01); *A61M 2005/3247* (2013.01); *A61M 2005/3267* (2013.01); *A61M 2205/581* (2013.01); *A61M 2205/583* (2013.01)

(56) References Cited

U.S. PATENT DOCUMENTS 7,704,237 B2 * 4/2010 Fisher et al. .................. 604/208
2003/0014019 A1 1/2003 Saied

OTHER PUBLICATIONS

International Preliminary Report on Patentability for Int. App. No. PCT/EP2011/060322, mailed Nov. 12, 2012.

* cited by examiner

SAFETY DEVICE FOR A PRE-FILLED SYRINGE AND INJECTION DEVICE

CROSS REFERENCE TO RELATED APPLICATIONS

The present application is a U.S. National Phase application pursuant to 35 U.S.C. §371 of International Application No. PCT/EP2011/060322 filed Jun. 21, 2011, which claims priority to European Patent Application No. 10168322.5 filed on Jul. 2, 2010. The entire disclosure contents of these applications are herewith incorporated by reference into the present application.

FIELD OF INVENTION

The present invention relates to safety devices that provide needle safety and more particularly to safety devices for pre-filled syringes. The safety device is adapted to avoid accidental needle stick injuries and needle injuries before, during and after an injection of a medication or drug contained in the pre-filled syringe. In particular, the safety device provides needle safety for a subcutaneous self-administrated injection or for an injection administered by a health-care professional. The present invention further relates to injection devices comprising a pre-filled syringe.

BACKGROUND

Pre-filled syringes that are filled with a selected dosage of a medication are well known injection devices for administering the medication to a patient. Safety devices for covering a needle of a pre-filled syringe before and after use are also well known. Typically, these devices comprise a needle shield that is either manually moved or moved by the action of a relaxing spring to surround the needle.

A different type of safety devices known in the state of the art solves the object of providing needle safety by arranging the pre-filled syringe movable relative to a body, whereas the pre-filled syringe is retracted into the body after the injection.

SUMMARY

It is an object of the present invention to provide an improved safety device for a pre-filled syringe.

It is a further object of the invention to provide an improved injection device comprising a pre-filled syringe that is safe to handle and in particular prevents accidental needle stick injuries.

The object is achieved by a safety device according to claim 1 and by an injection device according to claim 14.

Preferred embodiments of the invention are given in the dependent claims.

In the context of this patent, the terms distal and proximal are defined from the point of view of a person performing an injection. Consequently, a distal direction refers to a direction pointing towards the body of a patient receiving an injection and a distal end defines an end of an element that is directed towards the body of the patient. Respectively, the proximal end of an element or the proximal direction is directed away from the body of the patient receiving the injection and opposite to the distal end or distal direction.

A safety device for a pre-filled syringe comprises a hollow support body to retain the pre-filled syringe, a retaining collar and a rotating collar arranged within the support body. The retaining collar is releasably mounted to the support body. The rotating collar is slidable along an axial length of the support body and rotatable around a central axis of the safety device. The retaining collar is movable with respect to the support body in a proximal direction when the retaining collar is released from being mounted to the support body by the rotating collar.

The location and angular orientation of the rotating collar relative to the support body arms and activates safety features of the safety device, such as arming a release and retraction mechanism. The rotating collar releases the retaining collar from being mounted to the support body after a single injection stroke has been performed. With the pre-filled syringe mounted to the retaining collar, the release of the retaining collar and the following proximal movement of the retaining collar relative to the support body results in a retraction of the pre-filled syringe with respect to the support body. The rotating collar allows for a convenient use of the safety device avoiding accidental needle pricks caused by a hypodermic needle of the pre-filled syringe inserted into the support body of the safety device.

As the rotating collar is rotatable and slidable within the support body between different positions, a relative rotation of any external parts of the safety device during an injection is avoided. In particular when the hypodermic needle still penetrates the skin of a patient receiving the injection, unnecessary pain might be caused to the patient if complicated movements like rotation of external parts have to be executed to activate the safety features of the safety device. The safety features of the safety device according to the invention are conveniently activated by a user performing a single linear injection stroke.

The rotating collar comprises a central opening for the reception of the pre-filled syringe therein and at least one outwardly protruding guide pin that protrudes through a guide track formed into the support body. The guide pin moves within and along the guide track during the injection, whereas the guide track comprises an inclined section that is oriented at an acute angle relative to the central axis of the safety device. When the guide pin is moved along the inclined section, the rotating collar rotates within the support body around the central axis and changes its angular orientation. This change of angular orientation allows the rotating collar to bear against and release a retaining collar mounting the pre-filled syringe relative to the support body. The release of the retaining collar occurs automatically after a single linear injection stroke has been carried out. No additional interaction or attention is required from the user of the safety device performing the injection stroke to arm and activate the release and retraction mechanism. For safety reasons, the safety device is automatically prevented from being re-used after the single linear injection stroke has been carried out.

An outer body is manually moved relative to the support body by a user of the safety device performing the injection stroke. The outer body abuts the outwardly protruding guide pin, so that the rotating collar jointly moves together with the outer body parallel a central axis of the safety device and along a substantial axial length of the support body. This simple mechanism couples the linear axial movement of the outer body relative to the support body in particular during the injection stroke to the movement of the rotating collar within the support body, whereby the safety features of the safety device are armed and activated.

An inclined section of the guide track is oriented at an acute angle relative to the central axis. The guide pin protruding through the guide track is pushed by the outer body along the inclined section of the guide track, whereby the guide pin moves both in a lateral and in the axial direction parallel to the central axis. Simultaneously, the rotating collar rotates within the support body and changes its angular orientation relative to the support body, so that the guide pin is prevented to travel back into the inclined section of the guide track, whereby a re-usage of the safety device is prevented. Thus, the safety device is designed to be used in combination with disposable pre-filled syringes and prevents needle stick injuries with contaminated hypodermic needles.

The inclined section of the guide track is connected to a parallel section of the guide track extending parallel to the central axis by a narrowed section. The narrowed section is limited by a flexing gate element that is resiliently deflectable allowing for at least a one-way transition of the guide pin from the inclined section to the parallel section of the guide track. The guide pin is prevented to travel back into the inclined section from a proximal direction. The flexing gate element is an additional means to prevent the re-usage of the device.

In one embodiment of the invention, the safety device produces an audible feedback when the guide pin passes the flexing gate element in the narrowed section. Thus, the safety device generates a feedback indicating that the release and retraction mechanism is armed to allow for a retraction of the pre-filled syringe within the support body.

A spring is arranged within the support body that bears against the rotating collar, whereby the rotating collar is biased in a proximal direction. Initially, the spring is in a partially energized state. During the injection stroke, the rotating collar moves in the distal direction, whereby the spring energized and charged. The spring is thus fully charged only for a short period of time during the use of the safety device, so that the pre-filled syringe can be retracted by the action of the relaxing spring. The spring is only partially charged during shipment and storage of the safety device, which in turn avoids material fatigue and thus increases the shelf-life of safety device.

According to a further embodiment of the invention, the needle shield is slidably arranged within the support body. The spring is arranged within the support body between the rotating collar and the needle shield, so that the needle shield is biased in a distal direction. The needle shield surrounds the hypodermic needle before the injection to avoid or reduce a possible patient's fear of needles. The safety device is designed in a manner that the hypodermic needle of the pre-filled syringe is never exposed before or after the injection. The safety device is thus particularly suited for performing self-administered subcutaneous or intramuscular injections. Consequently, the user of the safety device and/or injection device can be one and the same person.

According to the same embodiment, the needle shield has a central aperture of variable diameter. Preferably, the needle shield is made from a flexible material. Before usage of the device a needle cap covering the hypodermic needle protrudes through the central aperture of the needle shield. After removal of the needle cap, the central aperture relaxes and relieves to form a central aperture of reduced diameter due to the memory of the flexible material of the needle shield. This central aperture of reduced diameter additionally reduces the risk of an inadvertent contact with the hypodermic needle. Furthermore, an axial distance by which the needle shield has to protrude the support body to ensure needle safety can be reduced.

Preferably, the needle shield is made by the process of a two-shot injection moulding. The combination of a relative rigid and a relative soft material allows the needle shield to retain its substantial cylindrical shape whilst being able to stretch over the needle cap.

According to another embodiment of the invention, the retaining collar comprises at least one ratchet arm that latches to a locking cut-out formed into the outer body to lock the retaining collar relative to the outer body. Thus, the retaining collar locked to the outer body can be released from being mounted to the support body and be moved in a proximal direction with respect to the support body by a proximal movement of the outer body. The outer body moves proximally by the action of the relaxing spring, whereas the biasing force of the relaxing spring is transferred to the outer body via the rotating collar and the guide pin abutting the outer body. In this embodiment of the invention, the retraction mechanism is advantageously combined with a locking feature of the outer body, so that a re-exposure of the hypodermic needle is prevented and a subsequent injection stroke following the first injection stroke is prevented.

According to the same embodiment of the invention, the outer body comprises a plurality of locking cut-outs that are axially displaced relative to each other. As the outer body is slid with respect to the support body to inject the medication, the ratchet arm locks into one of the locking cut-outs that corresponds to the axial displacement of the outer body with respect to the support body. The outer body is thus locked to the retaining collar. When the ratchet arm locks to the locking recess located at a proximal end of the outer body, the safety device automatically becomes needle safe after the safety device has been removed from the injection site.

According to yet another embodiment, a guide rail is formed into an inner surface of the outer body. The guide rail guides the guide pin in particular along the inclined section of the guide track to rotate the rotating collar within the support body, so that the release and retraction mechanism of the safety device is activated.

The guide rail comprises a first section that is oriented at an angle less than 90 degrees with respect to the central axis and a second section that substantially extends parallel to the central axis. The first section of the guide rail abuts the guide pin when the outer body is slid relative to support body to perform the injection stroke. The orientation of the first section relative to the central axis supports the rotating movement of the rotating collar within the support body.

An injection device comprises a pre-filled syringe retained in the support body of the safety device. The pre-filled syringe comprises a hypodermic needle attached to a distal end of the pre-filled syringe, a barrel with an inner cavity in fluid communication with the hypodermic needle and a piston fluid-tightly sealing a proximal end of the inner cavity. The pre-filled syringe is releasably mounted by the mounting means within the support body of the safety device, so that the pre-filled syringe can be retracted to cover the hypodermic needle after the injection. The injection device comprising the pre-filled syringe and the safety device combines the aforementioned advantages and avoids inadvertent needle sticks before, during and after an injection delivering the medication beneath the skin of a patient.

According to a possible embodiment, the ratchet arm locks into the locking cut-out that corresponds to a piston stroke length of the piston within the barrel of the pre-filled syringe as the outer body is slid with respect to the support body to inject the medication. A user performing the injection can visually verify which locking cut-out is occupied by the ratchet arm, which in turn indicates the piston stroke length and thus an amount of medication left in an inner cavity of the pre-filled syringe retained in the safety device.

Details of the present invention are described hereinafter. However, it should be understood that the detailed description and the specific examples indicate possible embodiments of the invention and are given by way of illustration only. Various changes and modifications of the illustrated embodiments within the spirit and scope of the invention are appreciated by those skilled in the art.

BRIEF DESCRIPTION OF THE DRAWINGS

The present invention will be better understood from the detailed description given in the following. The accompanying drawings are given for illustrative purposes only and do not limit the scope of the present invention.

Corresponding parts are marked with the same reference symbols in all figures.

DETAILED DESCRIPTION

Figure 1:
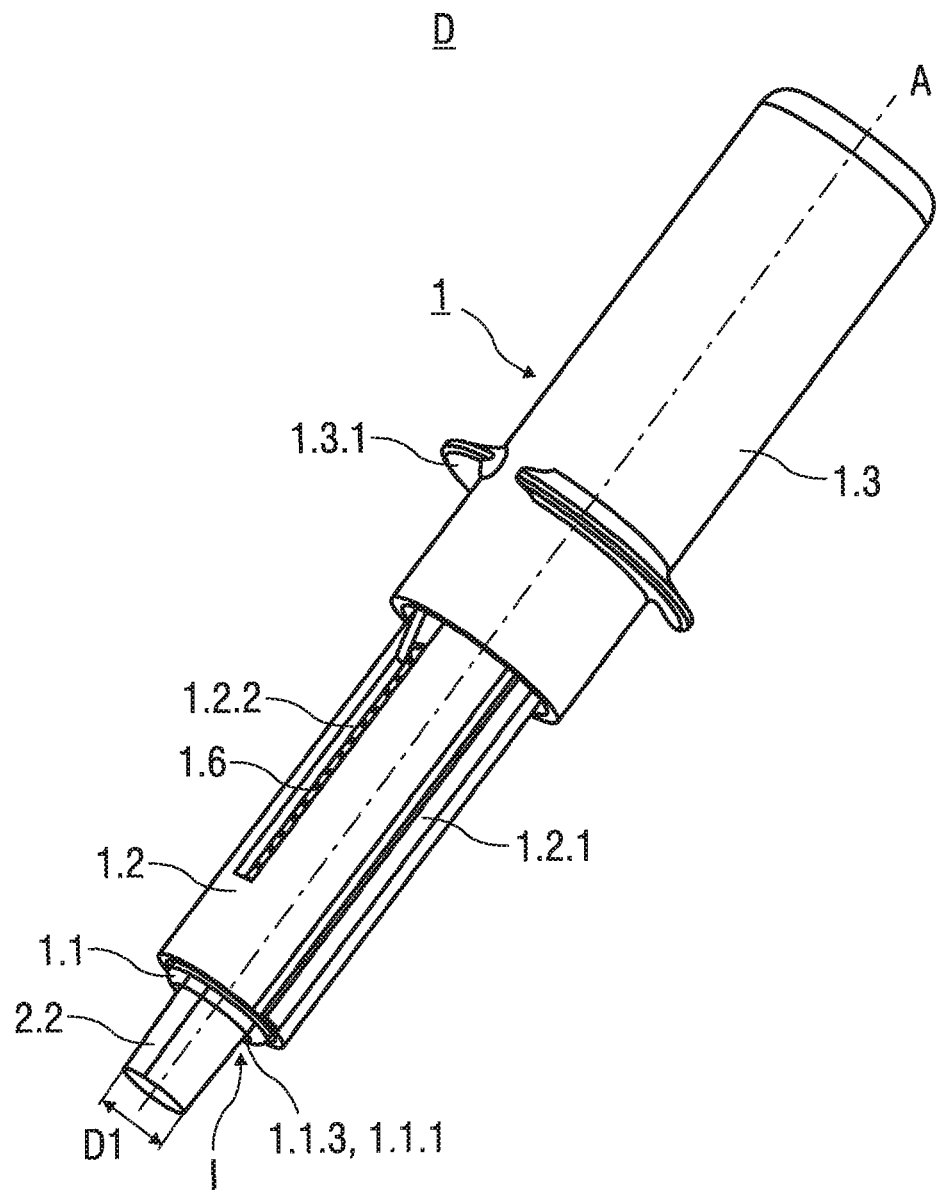
FIG. 1 shows a perspective view of an injection device according to a first embodiment of the invention in a packaged state.

FIG. 1 shows a perspective view of an injection device D with a safety device 1 according to a first embodiment of the invention. The injection device D is in a packaged state as it would be presented to an end-user.

The safety device 1 comprises a needle shield 1.1 that is substantially received within an open distal end of a tubular support body 1.2 prior to use of the safety device 1. A proximal end of the support body 1.2 is received in an open distal end of a hollow outer body 1.3, whereas the outer body 1.3 is slidable relative to the support body 1.2.

Two wing-shaped gripping means 1.3.1 protrude the outer body 1.3 in a radial outward direction perpendicular to a central axis A of the safety device 1. The gripping means 1.3.1 are moulded to opposite sides of the outer body 1.3. The gripping means 1.3.1 are designed to support a hand of a user of the safety device 1 during the injection stroke. Alternatively, the gripping means 1.3.1 may be designed as an annular flange.

The support body 1.2 comprises two longitudinal tongues 1.2.1 protruding opposite sides of the support body 1.2 in a radial outward direction. The longitudinal tongue 1.2.1 extends along a substantial length of the support body 1.2. Each longitudinal tongue 1.2.1 is received in a corresponding longitudinal groove 1.3.2 shown in FIGS. 4 and 7. The longitudinal groove 1.3.2 is formed into an inner surface of the outer body 1.3, so that a rotation of the outer body 1.3 relative to the support body 1.2 is prevented when the outer body 1.3 is moved relative to the support body 1.2.

At least one guide track 1.2.2 is formed into the support body 1.2 that accommodates a guide pin 1.4.1 extending radial outwardly from a rotating collar 1.4 arranged within the support body 1.2. The rotating collar 1.4 with the guide pin 1.4.1 is shown in detail in FIGS. 5A to 5C.

According to the first embodiment of the safety device 1 shown in FIG. 1, two guide tracks 1.2.2 are formed into opposite sides of the support body 1.2, whereas each guide track 1.2.2 receives a guide pin 1.4.1 of the rotating collar 1.4.

The injection device D comprises the safety device 1 with a pre-filled syringe 2 retained in the support body 1.2. The pre-filled syringe 2 comprises a hypodermic needle 2.1 that is covered by a needle cap 2.2 prior to use. The pre-filled syringe 2 is retained within the support body 1.2, so that the needle cap 2.2 covering the hypodermic needle 2.1 protrudes the support body 1.2 in a distal direction and can be easily gripped and manually removed before use of the injection device D.

Before the injection is carried out, the needle shield 1.1 is retained in a first position I within the support body 1.2, whereas the needle shield 1.1 in the first position I is substantially received within the support body 1.2. The needle shield 1.1 is made from flexible material, especially from two different plastics materials of different flexibility. Preferably, the needle shield 1.1 is constructed by the process of a two shot injection moulding.

The combination of a relative rigid and a relative material allows the needle shield 1.1 to retain its substantial cylindrical shape whilst being able to stretch over the needle cap 2.2 covering the hypodermic needle 2.1 of the pre-filled syringe 2 prior to use.

The distal end surface 1.1.1 comprises a central aperture 1.1.3 centred on the central axis A. The central aperture 1.1.3 has a diameter of variable width. In the packaged state shown in FIG. 1, the flexible material of distal end surface 1.1.1 is stretched over the needle cap 2.2 protruding the needle shield 1.1 in the distal direction. A first diameter D1 of the central aperture 1.1.3 corresponds to an outer diameter of the needle cap 2.2.

Additionally, the needle cap 2.2 frictionally engages the needle shield 1.1 to retain the needle shield 1.1 in the first position I.

Figure 2:
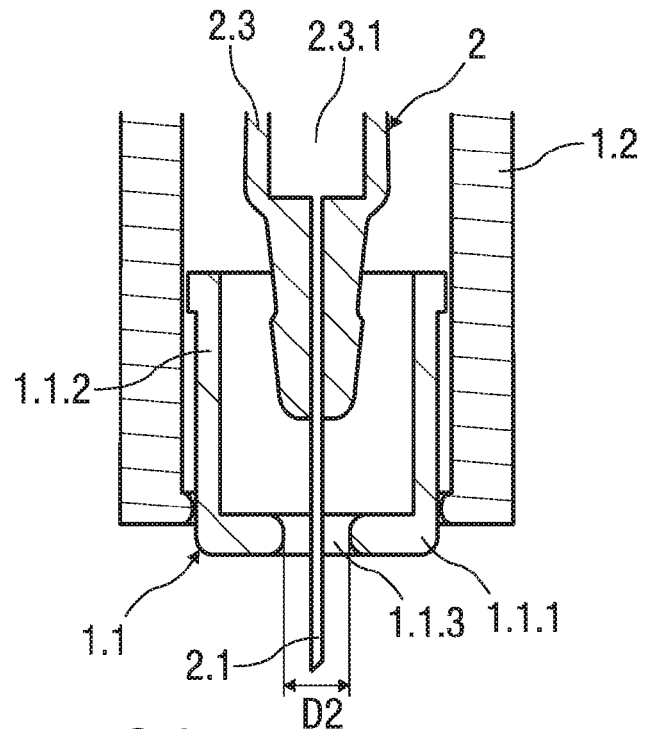
FIG. 2 shows a detailed view of a distal end of the support body with the needle shield retained therein.

After removal of the needle cap 2.2, the flexible material of the distal end surface 1.1.1 expands and unbends as a consequence of the stress relief, which results in a central aperture 1.1.3 with a reduced second diameter D2 as illustrated in FIG. 2.

FIG. 2 shows a detailed view of a distal end of the support body 1.2 with the needle shield 1.1 retained therein. The distal end surface 1.1.1 of the needle shield 1.1 is made from a flexible material. The lateral surface 1.1.2 of the substantially cylindrical needle shield 1.1 is made from a relative rigid and stiff plastics material.

During the injection, the needle shield 1.1 is moved to a second position II, so that the hypodermic needle 2.1 protrudes through the central aperture 1.1.3 with reduced second diameter D2 to dispose a medication beneath the skin of a patient.

Alternatively, the needle shield 1.1 may be retained in a second position II prior the injection, wherein the needle shield 1.1 in the second position II protrudes the support body 1.2 distally prior to use of the safety device 1.

Figure 3:
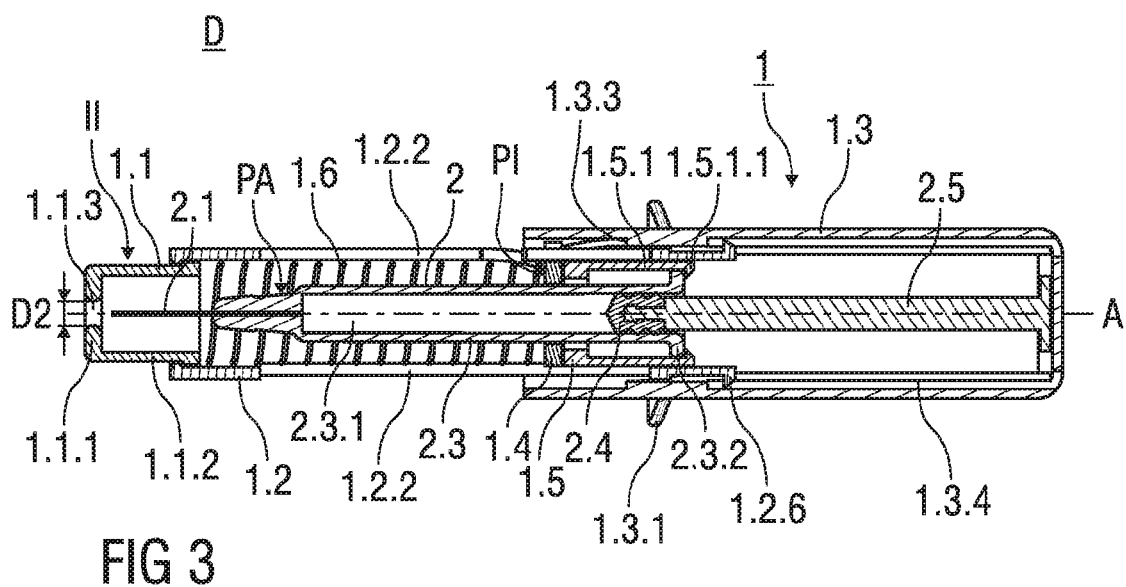
FIG. 3 shows a sectional view of the injection device according to the first embodiment before the injection.

FIG. 3 shows a sectional view of the injection device D according to the first embodiment before the injection. The rotating collar 1.4 is arranged within the support body 1.2, whereas the rotating collar 1.4 is slidable along a substantial axial length of the support body 1.2. The rotating collar 1.4 is retained in an initial position PI within the support body 1.2 adjacent to a retaining collar 1.5 releasably mounted to the proximal end of the support body 1.2. The retaining collar 1.5 mounts the pre-filled syringe 2 relative to the support body 1.2.

The pre-filled syringe 2 retained within the support body 1.2 comprises a barrel 2.3 with an inner cavity 2.3.1 containing a medication, a piston 2.4 fluid tightly sealing a proximal end of the inner cavity 2.3.1 and a piston rod 2.5 connected to the piston 2.4, whereas the piston 2.4 is movable at least in the distal direction by actuating the piston rod 2.5. A circumferential barrel collar 2.3.2 is formed to a proximal end of the barrel 2.3.

Alternatively, the piston rod 2.5 is arranged with the outer body 1.3 as one piece.

The barrel collar 2.3.2 protrudes in the radial outward direction. The retaining collar 1.5 comprises two opposing outer arms 1.5.1 that extend parallel to the central axis A. An inward projection 1.5.1.1 is formed to a proximal end of each outer arm 1.5.1. The inward projections 1.5.1.1 protrude in a radial inward direction and clamp to the barrel collar 2.3, so that a proximal movement of the pre-filled syringe 2 with respect to the retaining collar 1.5 is prevented.

A spring 1.6 is arranged within the support body 1.4 between the needle shield 1.1 and the rotating collar 1.4 in a partially energized state. The spring 1.6 bears against the needle shield 1.1 in the distal direction and against the rotating collar 1.4 in the proximal direction, so that needle shield 1.1 and rotating collar 1.4 is biased away from each other.

A guide rail 1.3.3 is formed into the inner surface of the outer body 1.3 that abuts the guide pin 1.4.1 protruding through the guide track 1.2.2 of the support body 1.2. The guide rail 1.3.3 guides the movement of the guide pin 1.4.1 along and within the guide track 1.2.2 when the outer body 1.3 is moved relative to the support body 1.2.

An inner axial recess 1.3.4 is formed into the inner surface of the outer body 1.3. The inner axial recess 1.3.4 extends parallel to the central axis A and over a substantial length of the outer body 1.3. An outwardly protruding guiding projection 1.2.6 connected to the support body 1.2 moves within and along the inner axial recess 1.3.4 to prevent a relative rotation between the outer body 1.3 and the support body 1.2 and to limit a proximal movement of the outer body 1.3 with respect to the support body 1.2.

Figure 4:
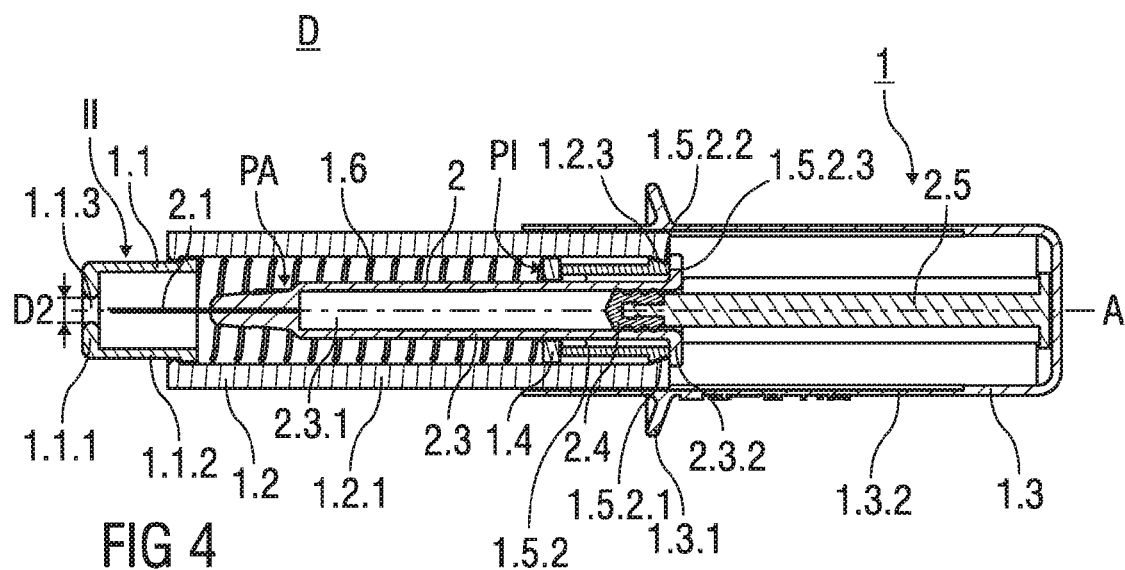
FIG. 4 shows a sectional view of the injection device according to the first embodiment and illustrates a cross-section perpendicular to the cross-section shown in FIG. 3.

FIG. 4 shows a sectional view of the injection device D according to the first embodiment and illustrates a cross-section perpendicular to the cross-section shown in FIG. 3. The retaining collar 1.5 comprises two inner arms 1.5.2 opposite to each other. The inner arms 1.5.2 extend parallel to the central axis A and are deflectable in at least the radial inward direction.

An outward projection 1.5.2.1 is formed to the proximal end of the inner arm 1.5.2. The outward projection 1.5.2.1 comprises an inclined outer surface 1.5.2.2 oriented at an acute angle relative to the central axis A that faces and abuts a corresponding inclined inner surface 1.2.3 formed to the proximal end of the support body 1.2. The inclined inner surface 1.2.3 and the inclined outer surface 1.5.2.2 are oriented in a manner that the inner arm 1.5.2 is deflected in a radial inward direction when the retaining collar 1.5 is moved with respect to the support body 1.2 in the proximal direction.

Before the injection, the pre-filled syringe 2 is retained within the support body 1.2 in an advanced position PA, in which the hypodermic needle 2.1 protrudes the support body 1.2 in the distal direction. The barrel collar 2.3.2 of pre-filled syringe 2 in the advanced position PA abuts the proximal end of the support body 1.2 and a proximal surface 1.5.2.3 of the outward projection 1.5.2 in the distal direction, so that a distal movement of the pre-filled syringe 2 with respect to the support body 1.2 is prevented.

Figures 5A, 5B, 5C:
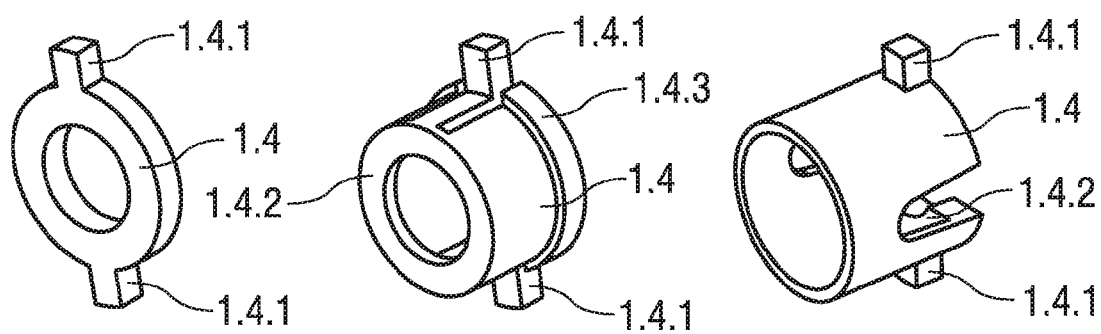
FIGS. 5A to 5C show perspective views of different embodiments of a rotating collar.

FIGS. 5A to 5C show perspective views of different embodiments of the rotating collar 1.4. The rotating collar 1.4 comprises a central opening 1.4.2 that comprises a diameter that corresponds to or is slightly bigger than a corresponding outer diameter of the barrel 2.3 of the pre-filled syringe 2, so that the rotating collar 1.4 can be moved along a substantial axial length of the barrel 2.3 and rotated relative to the pre-filled syringe 2 when the pre-filled syringe 2 is retained within the safety device 1.

FIG. 5A shows a ring-shaped rotating collar 1.4. Two guide pins 1.4.1 are formed to the rotating collar 1.4 at opposite sides. Each guide pin 1.4.1 extends in the radial outward direction.

FIGS. 5B and 5C show alternative tubular-shaped embodiments of the rotating collar 1.4. The rotating collar 1.4 has a shape similar to a hollow cylinder.

Additionally, the rotating collar 1.4 according to FIGS. 5B and 5C comprises a bearing surface 1.4.2 formed to the substantially cylindrical rotating collar 1.4. The spring 1.6 arranged within the support body 1.2 bears against the bearing surface 1.4.2 to bias the rotating collar in the proximal direction.

In the embodiment of the rotating collar 1.4 shown in FIG. 5B, the bearing surface 1.4.2 is formed to a distal end of the rotating collar 1.4 and has the shape of a circumferential and inwardly protruding collar. The rotating collar 1.4 comprises an outwardly protruding proximal rim 1.4.3 located at a proximal end of the rotating collar 1.4. The proximal rim 1.4.3 engages an inner surface of the support body 1.2 and is formed to the rotating collar 1.4 to minimize the friction between the rotating collar 1.4 and the support body 1.2 when the rotating collar 1.4 is moved within and/or rotated relative to the support body 1.2. The guide pin 1.4.1 is connected to the rotating collar 1.4 in a manner that allows for a resilient inward deflection of guide pin 1.4.1 when the rotating collar 1.4 is assembled within the support body 1.2.

FIG. 5C shows another alternative embodiment of the rotating collar 1.4. The bearing surface 1.4.2 is formed to an inner surface of the substantially cylindrical rotating collar 1.4 at the proximal end. The bearing surface 1.4.2 comprises two arc-shaped segments opposing each other. An outer surface of the rotating collar 1.4 is in contact with the inner surface of the support body 1.2 during use of the safety device 1. The outer surface of the rotating collar 1.4 has a substantially cylindrical shape and extends over an increased axial length in comparison to the embodiments shown in FIGS. 5A and 5B. This reduces the potential for the rotation collar 1.4 to jam in the support body 1.2.

Figure 6:
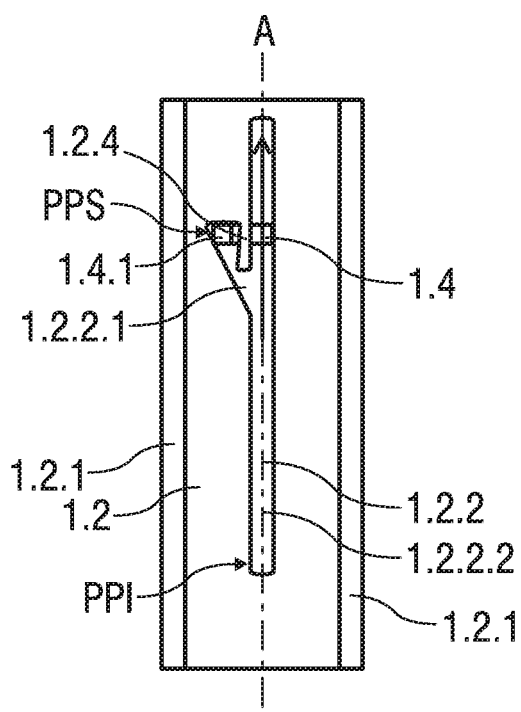
FIG. 6 shows a side view of a support body with a guide track.

FIG. 6 shows a side view of the support body 1.2 with the guide track 1.2.2. The guide pin 1.4.1 integral with the rotating collar 1.4 protrudes through the guide track 1.2.2. The guide track 1.2.2 has essentially a Y-shaped form and comprises an inclined section 1.2.2.1 oriented at an acute angle relative to the central axis A and an axial section 1.2.2.2 extending parallel to the central axis A along a substantial length of the support body 1.2. Alternatively, the guide track 1.2.2 may have a U-shaped form.

The inclined section 1.2.2.1 is connected to the axial section 1.2.2.2 by a narrowed section that is limited by a flexing gate element 1.2.4 that protrudes into the guide track 1.2.2. The flexing gate element 1.2.4 is resiliently deflectable in a lateral direction perpendicular to the central axis A in at least one direction to allow the guide pin 1.4.1 to pass from the inclined section 1.2.2.1 to the axial section 1.2.2.2 of the guide track 1.2.2.

Before the injection, the guide pin 1.4.1 is retained in a start position PS located at a proximal end of the inclined section 1.2.2.1, so that the rotating collar 1.4 is retained in the initial position PI within the support body 1.2.

The guide rail 1.3.3 formed into the inner surface of the outer body 1.3 abuts the guide pin 1.4.1 during the injection to move and guide the guide pin 1.4.1 along the guide track 1.2.2.

Figure 7:
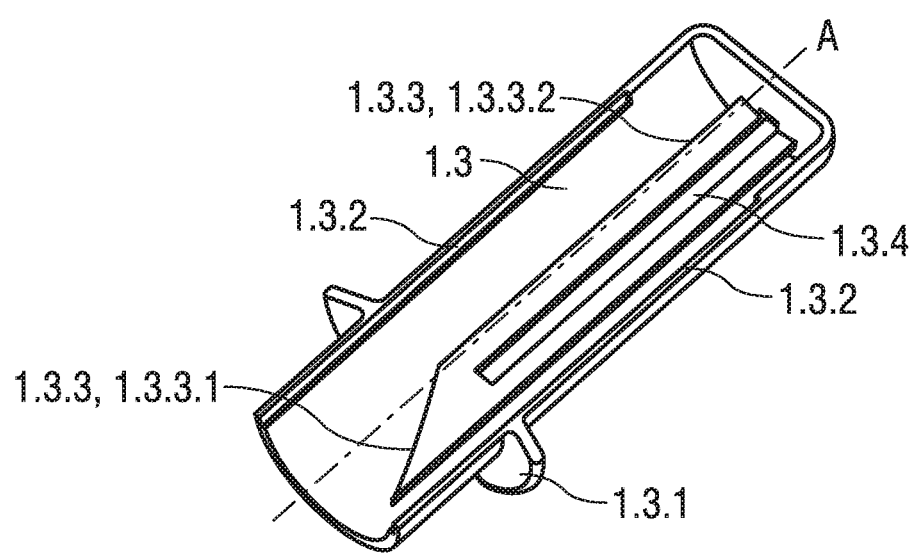
FIG. 7 shows details of an inner surface of an outer body of the safety device.

FIG. 7 shows details of the inner surface of the outer body 1.3. In FIG. 7, the outer body 1.3 is shown cut open along the longitudinal grooves 1.3.2 for better illustration of the inner features of the outer body 1.3.

The guide rail 1.3.3 formed into the inner surface of the outer body 1.3 comprises a first section 1.3.3.1 that is oriented at an angle less than 90 degrees and a second section 1.3.3.2 that extends essentially parallel to the central axis A. The first section 1.3.3.1 of the guide rail 1.3.3 abuts the guide pin 1.4.1 of the rotating collar 1.4.

The injection is carried out as follows: The user performing the injection manually removes the needle cap 2.2, as shown in FIG. 1, protruding a distal end of the safety device 1, whereby the distal end surface 1.1.1 relaxes and unbends to form the central aperture 1.1.3 of reduced diameter D2, as illustrated in FIG. 3.

Upon removal of the needle cap 2.2, the spring 1.6 relaxes and moves the needle shield 1.1 from the first position I to the second position II, so that the hypodermic needle 2.1 is surrounded by the needle shield 1.1.

Alternatively, the needle shield 1.1 may be retained in the second position II prior the injection.

The injection device D comprising the safety device 1 with the pre-filled syringe 2 retained therein is then put onto a skin surface of a patient, so that the central axis A of the safety device 1 is orientated essentially perpendicular to the skin surface of a patient and the distal end surface 1.1.1 of the needle shield 1.1 rests onto the skin surface of the patient. A proximal end section of the outer body 1.3 is gripped and pushed distally parallel to the central axis A towards the skin surface to carry out the injection stroke.

The distal surface 1.1.1 is pressed proximally against the biasing force of the spring 1.6 whereby the needle shield 1.1 moves from the second position II to the first position I and the hypodermic needle 2.1 penetrates the skin of the patient. At the same time, the closed proximal end of the outer body 1.3 abuts the proximal end of the piston rod 2.5, so that the piston 2.4 can be pushed in a distal direction by moving the outer body 1.3 towards the skin surface to expel the medication contained in the inner cavity 2.3.1 through the hypodermic needle 2.1.

As shown in FIG. 6, the first section 1.3.3.1 of the guide rail 1.3.3 abuts the guide pin 1.4.1 that is located in the start position PPS within the guide track 1.2.2 at the beginning of the injection stroke. The guide pin 1.4.1 in the start position PPS retains the rotating collar 1.4 within the support body 1.2 in the initial position PI. The outer body 1.3 is pushed distally towards the skin surface, whereby the guide pin 1.4.1, the rotating collar 1.4 and the outer body 1.3 jointly move in the distal direction.

The guide pin 1.4.1 is pushed along the inclined section 1.2.2.1 of the guide track 1.4, whereby the rotation collar 1.4 rotates within the support body 1.2 around the central axis A and changes its angular orientation relative to the support body 1.2. As indicated in FIG. 8, the guide pin 1.4.1 is pushed past the flexing gate element 1.2.4 and passes the section of narrowed width connecting the inclined section 1.2.2.1 and the axial section 1.2.2.2 of the guide track 1.2.2, whereby the flexing gate element 1.2.4 is resiliently and laterally deflected.

In a possible embodiment of the invention, the safety device 1 produces an audible feedback when the guide pin 1.4.1 passes the flexing gate element 1.2.4 to indicate that the release and retraction mechanism of the safety device 1 is activated. The audible feedback can be produced by the resiliently deflectable flexing gate element 1.2.4 that snaps back into place when the guide pin 1.4.1 passed the narrowed section of the guide track 1.2.2.

The guide pin 1.4.1 is further pushed along the axial section 1.2.2.2 in the distal direction towards an intermediate position PPI by the distal movement of the outer body 1.3. Simultaneously, the rotating collar 1.4 is pushed distally against the biasing force of the spring 1.6 towards a distal position PD and the medication contained in the inner cavity 2.3.1 is disposed beneath the skin of the patient.

Figure 8:
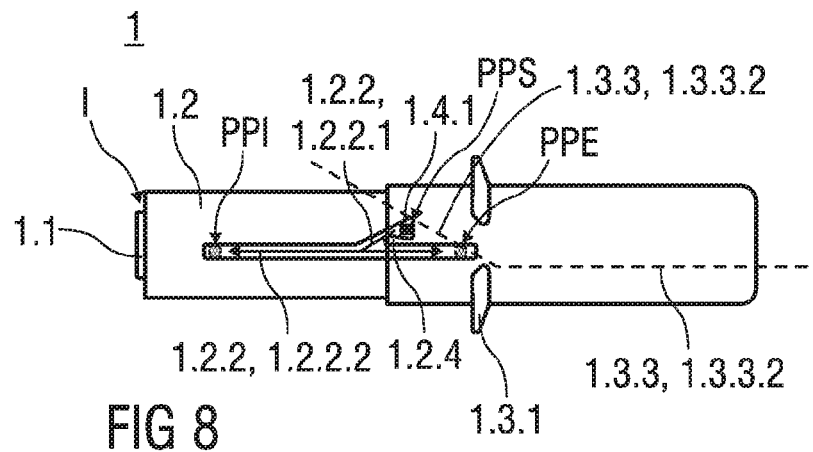
FIG. 8 illustrates schematically the movement of a guide pin within the guide track.

FIG. 8 illustrates schematically the movement of the guide pin 1.4.1 within the guide track 1.2.2. For illustrative purposes, the extension of the guide rail 1.3.3 is indicated by a doted line.

When the guide pin 1.4.1 reaches the intermediate position PPI located at the distal end of the axial section 1.2.2.2 of the guide track 1.2.2 at the end of the injection stroke, the medication has been completely expelled through the hypodermic needle 2.1. The rotating collar 1.4 is retained in the distal position PD corresponding to the intermediate position PPI of the guide pin 1.4.1 within the guide track 1.2.2.

Figure 9:
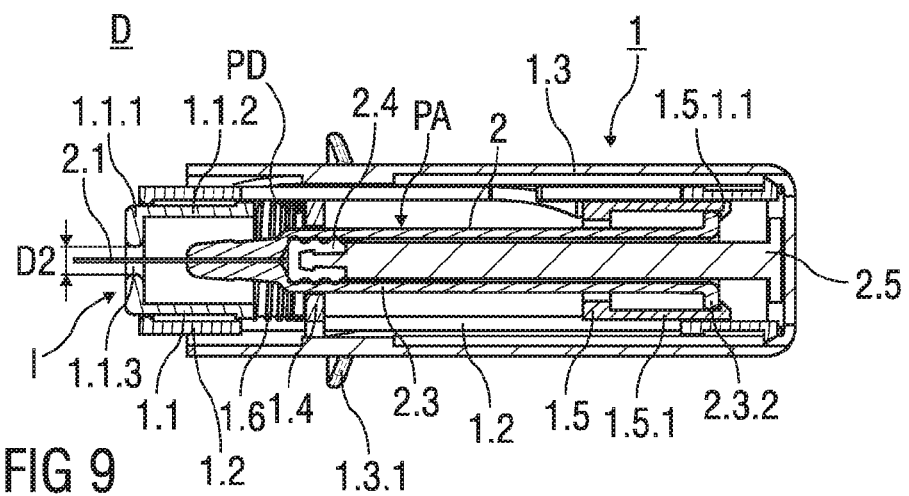
FIG. 9 shows a sectional view of an injection device at the end of the injection stroke corresponding to the cross-section shown in FIG. 4.

FIG. 9 shows a sectional view of the injection device D with a safety device 1 at the end of the injection stroke corresponding to the cross-section shown in FIG. 4. With the needle shield 1.1 retained in the first position I and the rotating collar 1.4 positioned in the distal position PD located in proximity of the distal end of the support body 1.2, the spring 1.6 is fully charged and fully energized. The user performing the injection therefore has to counteract the biasing force exerted on the needle shield 1.1 and the rotating collar 1.4 by the spring 1.6 to hold the needle shield 1.1 in the first position I and the rotating collar 1.4 in the distal position PD. This is done by pushing the outer body 1.3 in the distal direction while the distal end surface 1.1.1 rests onto the skin surface of the patient.

Upon removal of the injection device D from the injection site, the spring 1.6 relaxes and moves the needle shield 1.1 to the second position II. At the same time, the rotating collar 1.4 is moved by the action of the relaxing spring 1.6 in the proximal direction towards a proximal position PP. As the guide pin 1.4.1 of the rotating collar 1.4 abuts the guide rail 1.3.3, the outer body 1.3 jointly moves with the rotating collar 1.4 in the proximal direction with respect to the support body 1.2.

As best seen in FIG. 8, the guide pin 1.4.1 travels from the intermediate position PPI along the axial section 1.2.2.2 of the guide track 1.2.2 in the proximal direction towards an end position PPE. The flexing gate element 1.2.4 prevents the guide pin 1.4.1 from re-entering the start position PPS, so that the guide pin 1.4.1 travels further in the proximal direction until the guide pin 1.4.1 abuts a proximal end of the guide track 1.2.2, so that the guide pin 1.4.1 is retained in the end position PPE.

The rotating collar 1.4 jointly moves within the support body 1.2 in the proximal direction. On the way towards the proximal position PP corresponding to the end position PPE of the guide pin 1.4.1, the rotating collar 1.4 bears against the retaining collar 1.5 in the proximal direction. The inclined inner surface 1.2.3 of the support body 1.2 abutting the inclined outer surface 1.5.2.2 causes the inner arm 1.5.2 of the retaining collar 1.5 to be radial inwardly deflected, whereby the retaining collar 1.5 is released from being mounted within the support body 1.2. The retaining collar 1.5 is pushed further in the proximal direction, whereby the pre-filled syringe 2 mounted to the retaining collar 1.5 is retracted.

Figure 10:
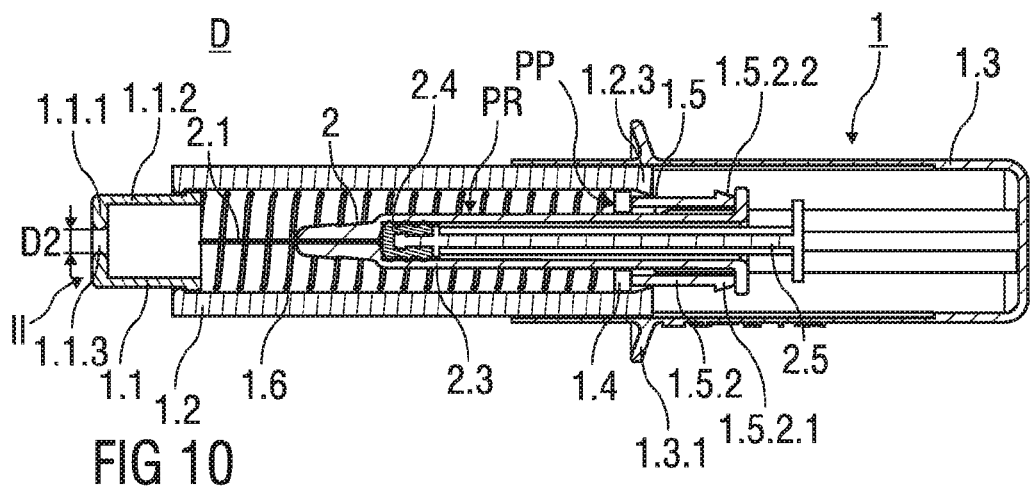
FIG. 10 shows a sectional view of the injection device in a final state after the injection has been performed corresponding to the cross-section shown in FIG. 4.

FIG. 10 shows a sectional view of the injection device D with the safety device 1 in a final state after the injection has been performed. The rotating collar 1.4 reaches the proximal position PP, wherein the retaining collar 1.5 mounting the pre-filled syringe 2 protrudes the support body 1.2 in the proximal direction. The pre-filled syringe 2 is retained in a retracted position PR, whereby the hypodermic needle 2.1 of the pre-filled syringe 2 is surrounded by the support body 1.2. A proximal part of the pre-filled syringe 2 in the retracted position PR is covered by the hollow outer body 1.3. A re-exposure of the hypodermic needle 2.1 is prevented by the biasing force exerted onto the rotating collar 1.4 by the spring 1.6 in the proximal direction that is transferred to the pre-filled syringe 2 via the retaining collar 1.5.

FIGS. 11 to 14 show an injection device D with a safety device 1 according to a second embodiment of the invention.

Figure 11:
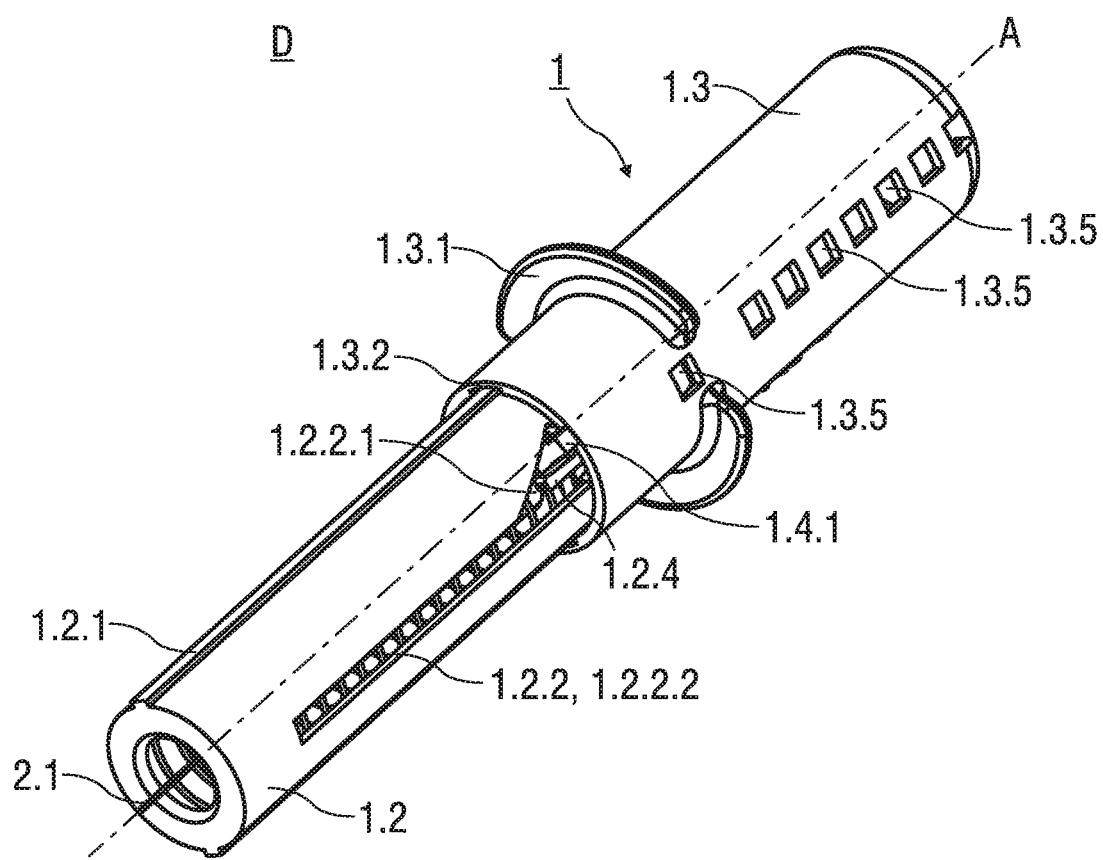
FIGS. 11 to 14 show perspective and sectional views of an injection device according to a second embodiment of the invention.

FIG. 11 shows a perspective view of the injection device D with the safety device 1 according to the second embodiment before the injection. The outer body 1.3 comprises opposite longitudinal grooves 1.3.2 formed by outwardly protruding longitudinal bulge in the surface of the outer body 1.3.

A plurality of locking cut-outs 1.3.5 are formed into the outer body 1.3 that are aligned parallel to the central axis A and axially displaced from each other.

Figure 12:
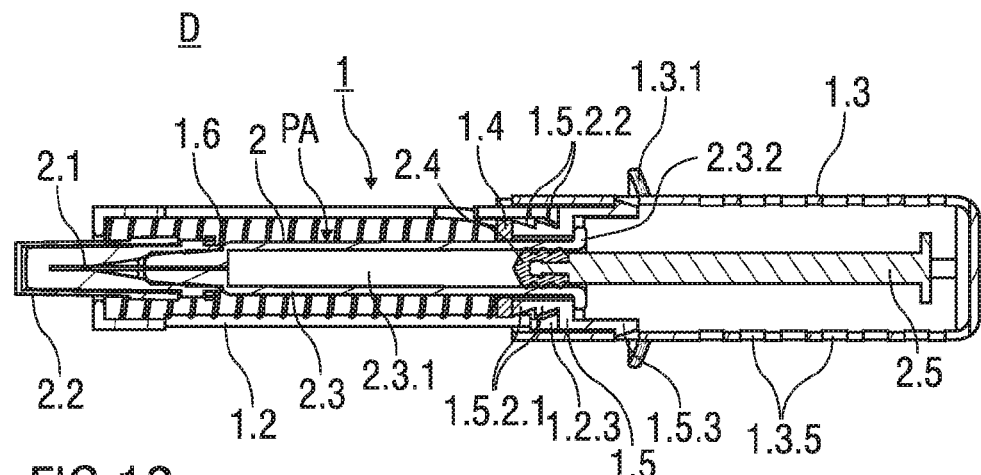

FIG. 12 shows a sectional view of the safety device 1 according to the second embodiment prior to use. The needle cap 2.2 covering the hypodermic needle 2.1 protrudes the support body 1.2 in the distal direction.

The retaining collar 1.5 comprises a ratchet arm 1.5.3 that latches to the locking cut-out 1.3.5 located at a distal end of the outer body 1.3, whereby an axial displacement of the retaining collar 1.5 with respect to the outer body 1.3 in the distal direction is prevented and an axial displacement of the retaining collar 1.5 with respect to the outer body 1.3 in the proximal direction is allowed.

Furthermore, the retaining collar 1.5 comprises a plurality of outward projections 1.5.2.1 that are axially displaced from each other.

The spring 1.6 arranged within the support body 1.2 bears against a distal inner surface of the support body 1.2 and the rotating collar 1.4 to bias the rotating spring 1.6 with respect to the support body 1.2 in a proximal direction.

Figure 13:
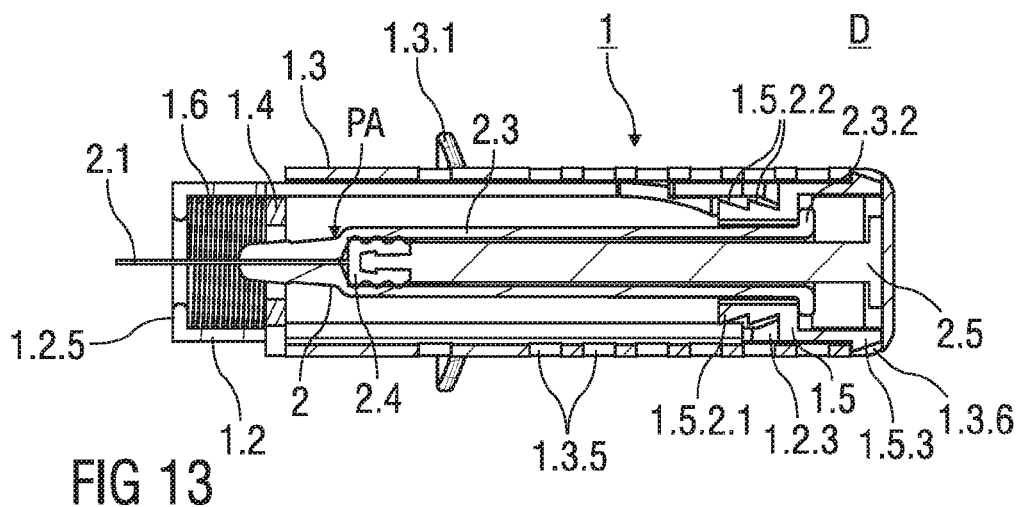
Figure 14:
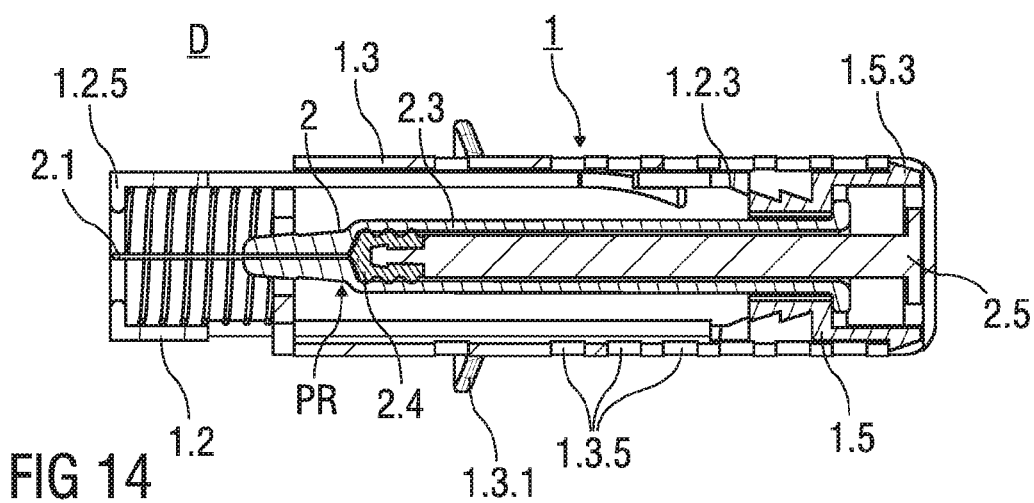

FIG. 13 shows the injection device D according to the second embodiment at the end of the injection stroke. The spring 1.6 is fully charged and fully energized.

The injection device D with the safety device 1 according to the second embodiment is used in an injection as follows: After removal of the needle cap 2.2, the hypodermic needle 2.1 protruding the support body 1.2 penetrates the skin of the patient at the injection site.

A distal end surface 1.2.5 of the support body 1.2 rests on the skin of the patient during the injection. The outer body 1.3 is moved towards the skin surface of the patient in the distal direction, whereby the medication contained in the inner cavity 2.3.1 is expelled.

During the distal movement of the outer body 1.3 with respect to the support body 1.2 and the retaining collar 1.5 releasably affixed to the distal end of the support body 1.2, the ratchet arm 1.5.3 latches to one of the locking cut-outs 1.3.5 corresponding to the piston stroke length of the piston 2.4 within the barrel 2.3. The user can visually confirm which of the locking cut-outs 1.3.5 is occupied from outside, and thus gets an indication of the displacement of the piston 2.4 within the barrel 2.3 and correspondingly an indication of an amount of medication left in the inner cavity 2.3.1 of the barrel 2.3.

For clear visual indication, the ratchet arm 1.5.3 may be coloured differently from the outer body 1.3.

The interaction of the ratchet arm 1.5.3 with the locking cut-out 1.3.5 blocks a proximal movement of the outer body 1.3 with respect to the retaining collar 1.5. Therefore, the retaining collar 1.5 is released from being mounted to the support body 1.2 when the outer body 1.3 is moved with respect to the support body 1.2 in the proximal direction.

FIG. 13 shows the injection device D with the safety device 1 at the end of the injection stroke. The spring 1.6 fully charged. When the injection device D is removed from the injection site, the spring 1.6 relaxes and moves the rotating collar 1.4 in the proximal direction. At the same time, the outer body 1.3 locked to the retaining collar 1.5 is moved proximally, as the guide pin 1.4.1 of the rotating collar 1.4 abuts the guide rail 1.3.3 formed into inner surface of the outer body 1.3. The retaining collar 1.5 is released from being mounted to the outer body 1.3 and moved proximally, whereby the pre-filled-syringe 2 is retracted to the retracted position PR shown in FIG. 14.

The invention claimed is:

1. A safety device for a pre-filled syringe, comprising
   a hollow support body to retain the pre-filled syringe therein,
   a retaining collar releasably mounted to the support body and
   a rotating collar comprising a central opening for the reception of the prefilled syringe and at least one outwardly protruding guide pin that protrudes through a guide track formed into the support body,
   a guide rail formed into an inner surface of an outer body,
   whereas the guide track comprises an inclined section and an axial section connected therewith,
   whereas the rotating collar is arranged within the support body and slidable along an axial length of the support body and rotatable around a central axis of the safety device and whereas the retaining collar is movable with respect to the support body in a proximal direction when the retaining collar is released from being mounted to the support body by the rotating collar.

2. A safety device according to claim 1, characterized in that an outer body slidably arranged relative to the support body abuts the outwardly protruding guide pin, so that the rotating collar jointly moves together with the outer body along a substantial axial length of the support body.

3. A safety device according to claim 1, characterized in that the inclined section of the guide track is oriented at an acute angle relative to the axial section of the guide track, whereas the inclined section is connected to the axial section by a narrowed section limited by a flexing gate element that is resiliently deflectable.

4. A safety device according to claim 3,
   characterized in that the safety device produces an audible feedback when the guide pin passes the narrowed section limited by the flexing gate element.

5. A safety device according to claim 1, characterized in that the rotating collar is biased in the proximal direction by a spring arranged within the support body.

6. A safety device according to claim 5, characterized in that a needle shield is slidably arranged relative to the support body, whereas the needle shield is biased in a distal direction by the spring.

7. A safety device according to claim 6, characterized in that the needle shield has a central aperture of variable diameter.

8. A safety device according to claim 6, characterized in that the needle shield is made by the process of a two-shot injection moulding.

9. A safety device according to claim 1, characterized in that the retaining collar comprises at least one ratchet arm that latches to a locking cut-out formed into an outer body to lock the retaining collar relative to the outer body.

10. A safety device according to claim 9, characterized in that the outer body comprises a plurality of locking cut-outs that are axially displaced relative to each other.

11. A safety device according to claim 1, characterized in that the guide rail comprises a first section that is oriented at an angle less than 90 degrees with respect to the central axis and a second section that substantially extends parallel to the central axis.

12. An injection device comprising a safety device and a pre-filled syringe, wherein the safety device comprises
- a hollow support body to retain the pre-filled syringe therein,
- a retaining collar releasably mounted to the support body and
- a rotating collar arranged within the support body comprising a central opening for the reception of the prefilled syringe and at least one outwardly protruding guide pin that protrudes through a guide track formed into the support body,
- a guide rail formed into an inner surface of an outer body,
- whereas the guide track comprises an inclined section and an axial section connected therewith,
- wherein the rotating collar is slidable along an axial length of the support body and rotatable around a central axis of the safety device and wherein the retaining collar is movable with respect to the support body in a proximal direction when the retaining collar is released from being mounted to the support body by the rotating collar,
- and wherein the pre-filled syringe is retractable into the support body from an advanced position to a retracted position, in which the hypodermic needle is surrounded by the support body.

13. The injection device according to claim 12, characterized in that the retaining collar comprises at least one ratchet arm that latches to a locking cut-out formed into an outer body to lock the retaining collar relative to the outer body.

14. A safety device according to claim 13, characterized in that the outer body comprises a plurality of locking cut-outs that are axially displaced relative to each other.

15. An injection device according to claim 14, characterized in that the ratchet arm and the plurality of locking cut-outs visually indicate an amount of a medication contained in an inner cavity.

* * * * *